(12) United States Patent
Friedman

(10) Patent No.: US 8,016,218 B1
(45) Date of Patent: Sep. 13, 2011

(54) LINEAR SPECIMEN SHAKER

(76) Inventor: Mitchell Friedman, Randallstown, MD (US)

( * ) Notice: Subject to any disclaimer, the term of this patent is extended or adjusted under 35 U.S.C. 154(b) by 0 days.

(21) Appl. No.: 13/065,181

(22) Filed: Mar. 16, 2011

(51) Int. Cl.
*B02C 17/24* (2006.01)

(52) U.S. Cl. ............ 241/175; 241/2; 366/110; 366/211; 366/212

(58) Field of Classification Search .............. 241/2, 170, 241/175; 366/208, 110, 212, 211, 216
See application file for complete search history.

(56) References Cited

U.S. PATENT DOCUMENTS

| | | | |
|---|---|---|---|
| 1,756,325 A | 4/1930 | Williams | |
| 2,198,637 A | 4/1930 | Smith | |
| 1,945,015 A | 1/1934 | Wurzbach et al. | |
| 2,247,978 A | 7/1941 | Van Arkel | |
| 2,255,799 A | 9/1941 | Meinzer | |
| 2,356,004 A | 8/1944 | Price | |
| 2,539,391 A | 1/1951 | Alvord | |
| 2,895,064 A | 7/1959 | Hoff et al. | |
| 2,900,138 A | 8/1959 | Strate | |
| 2,919,215 A | 12/1959 | Neuhaus et al. | |
| 3,106,652 A | 10/1963 | Burt | |
| 3,108,408 A | 10/1963 | Dahlquist et al. | |
| 3,155,853 A | 11/1964 | Spurlin et al. | |
| 3,310,292 A | 3/1967 | Moore | |
| 3,316,470 A | 4/1967 | Scott | |
| 3,465,974 A | 9/1969 | Eckert | |
| 3,601,372 A | 8/1971 | Harmes | |
| 3,635,446 A | 1/1972 | Kurosawa et al. | |
| 3,637,190 A | 1/1972 | Isaacson | |
| 3,769,758 A | 11/1973 | McDonald | |
| 3,876,379 A | 4/1975 | Ghim | |
| 3,978,623 A | 9/1976 | Smith | |
| 4,061,315 A | 12/1977 | Eitzen et al. | |
| 4,102,649 A | 7/1978 | Sasaki | |
| 4,118,801 A | 10/1978 | Kraft et al. | |
| 4,183,677 A | 1/1980 | de Bruyne | |
| 4,202,634 A | 5/1980 | Kraft et al. | |
| 4,264,559 A | 4/1981 | Price | |
| 4,305,668 A | 12/1981 | Bilbrey | |
| 4,356,911 A | 11/1982 | Brown | |
| 4,422,768 A | 12/1983 | Solomon | |

(Continued)

FOREIGN PATENT DOCUMENTS

FR 2804047 A1 1/2000

OTHER PUBLICATIONS

Retsch GmBH, Size Reduction and Homogenization with Mixer Mills, 2009.

(Continued)

*Primary Examiner* — Mark Rosenbaum
(74) *Attorney, Agent, or Firm* — Whiteford, Taylor & Preston LLP

(57) ABSTRACT

Disclosed is a linear shaker apparatus capable of effectively mixing a wide variety of large volume liquid samples that provides a near linear mixing motion so as to allow for the easy break up of solids suspended in the fluid sample. The longer shaking distances and slower operating speeds employed by the linear shaker described herein, which resembles the motion a scientist or lab technician might employ when shaking such a vial by hand, does not lend itself to the electromagnetic technique employed in various prior art shakers. The linear shaker described herein employs an electric motor and linkage that allows varying the speed and stroke of the mixing operation to accommodate different laboratory protocols.

9 Claims, 10 Drawing Sheets

U.S. PATENT DOCUMENTS

| | | | |
|---|---|---|---|
| 4,610,546 | A | 9/1986 | Intraub |
| 4,619,532 | A | 10/1986 | Schmidt |
| 4,688,727 | A | 8/1987 | Sijsling |
| 4,702,610 | A | 10/1987 | Reynolds |
| 4,870,982 | A | 10/1989 | Liu |
| 5,060,151 | A | 10/1991 | Mikyska et al. |
| 5,153,136 | A | 10/1992 | Vandenburgh |
| 5,261,540 | A | 11/1993 | Sijsling |
| 5,427,451 | A | 6/1995 | Schmidt |
| 5,593,228 | A | 1/1997 | Tannenbaum |
| 5,608,693 | A | 3/1997 | Richards |
| 5,821,657 | A | 10/1998 | Falconer et al. |
| 5,921,477 | A | 7/1999 | Tomes et al. |
| 6,508,582 | B2 | 1/2003 | Friedman |
| 6,579,002 | B1 | 6/2003 | Bartick et al. |
| 6,659,637 | B2 | 12/2003 | Friedman |
| 6,880,771 | B2 | 4/2005 | Deppermann |
| 6,886,764 | B2 | 5/2005 | Mashburn et al. |
| 7,210,843 | B2 * | 5/2007 | Friedman ............ 366/110 |
| 7,524,104 | B2 | 4/2009 | Malasky et al. |
| 2003/0081499 | A1 | 5/2003 | Friedman |
| 2007/0036025 | A1 | 2/2007 | Friedman |
| 2010/0181402 | A1 | 7/2010 | Maler et al. |

OTHER PUBLICATIONS

Retsch GmBH, Size Reduction and Homogenization with Ball Mills, 2008.

Alliance Analytical, Inc., Oscillating Mixer Mill MM 400.

Troemner, Talboys High Throughput Homogenizers by Troemner, Dec. 10, 2010.

Talboys, Instruction Manual Talboys High Trhoughput Homogenizer, 2009.

* cited by examiner

US 8,016,218 B1

LINEAR SPECIMEN SHAKER

FIELD OF THE INVENTION

This invention relates generally to mixing and shaking devices, and more particularly to vial shakers capable of near-linear shaking of large volumes (e.g., up to at least 50 ml) of liquids with intermixed solids to aid in breaking up solids and mixing the vial contents.

BACKGROUND

Mixing and shaking devices are widely used in a variety of laboratory applications, and may, for instance, be used in the food safety and water safety industries to test various samples. At times, such samples may initially include undissolved solids that will need to be broken up during the mixing operation. For instance, many test requirements for determining the presence of harmful chemicals, pesticides, bacteria, etc., require that larger volumes of liquid be shaken together with amounts of soil and/or vegetable matter. When shaking a mixture containing solids, it may also be desirable to break up the solids by employing a metal or ceramic ball or cylinder inside the sample tube being used to assist in macerating the solids in order to improve any chemical reaction.

While compact shakers have been available in the past for processing biological specimens in microplates, there exists a need for a shaker capable of effectively mixing larger volumes, for example up to 50 ml fluid samples, as may be required in food safety and water safety tests and that will sufficiently mix samples even when solids are present in the samples.

Linear, or essentially linear, shaking is desirable in the above instance because the relatively heavy ball or cylinder introduced to aid in breaking up the mixture works best when shaken rapidly in this essentially straight line motion. The heavy mixing ball or cylinder (if employed) can be driven from one end of the liquid containing specimen tube to the other completely breaking up the contained solids uniformly.

Larger specimens require a shaker that is well-balanced and that particularly properly balances forces on the apparatus during a mixing operation so as to minimize vibration and noise of the overall apparatus. It is desirable, therefore, to achieve a balance that can simultaneously maximize mixing while minimizing vibration and noise of the apparatus as a whole, without increasing the mass of the apparatus beyond a reasonable size suitable for laboratory use.

Moreover, various specimens have varied mixing requirements. Little prior success has been achieved in providing easily adjustable mixing apparatus for large volumes of liquid.

SUMMARY OF THE INVENTION

Disclosed is a linear shaker apparatus capable of effectively mixing a wide variety of large volume liquid samples that provides a near linear mixing motion so as to allow for the easy break up of solids suspended in the fluid sample. The longer shaking distances and slower operating speeds employed by the linear shaker described herein, which resembles the motion a scientist or lab technician might employ when shaking such a vial by hand, does not lend itself to the electromagnetic or other mechanical or electromechanical techniques employed in various prior art shakers. The linear shaker described herein employs an electric or other type of motor and linkage that allows varying the speed and stroke of the mixing operation to accommodate different laboratory protocols.

With regard to certain aspects of a particularly preferred embodiment of the invention, a specimen shaker is provided comprising a base having a first pivot connection and a second pivot connection, a first pivot arm pivotably connected to the base at the first pivot connection and having a first end located adjacent the first pivot connection and a second end opposite the first end, a second pivot arm pivotably connected to the base at the second pivot connection and having a first end located adjacent the second pivot connection and a second end opposite the first end, a first specimen holder attached to the first pivot arm at the second end of the first pivot arm and configured to shake a specimen therein in a direction generally perpendicular to the first pivot arm, a second specimen holder attached to the second pivot arm at the second end of the second pivot arm and configured to shake a specimen contained therein in a direction generally perpendicular to the second pivot arm, a drive affixed to the base and having a crank shaft, a first connecting arm extending between the crank shaft and the first pivot arm, and a second connecting arm extending between the crank shaft and the second pivot arm, wherein rotation of the crank shaft causes each of the first pivot arm and second pivot arm to pivot about the first pivot connection and the second pivot connection, respectively.

BRIEF DESCRIPTION OF THE DRAWINGS

The numerous advantages of the present invention may be better understood by those skilled in the art by reference to the accompanying figures in which.

DETAILED DESCRIPTION OF THE PREFERRED EMBODIMENTS

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
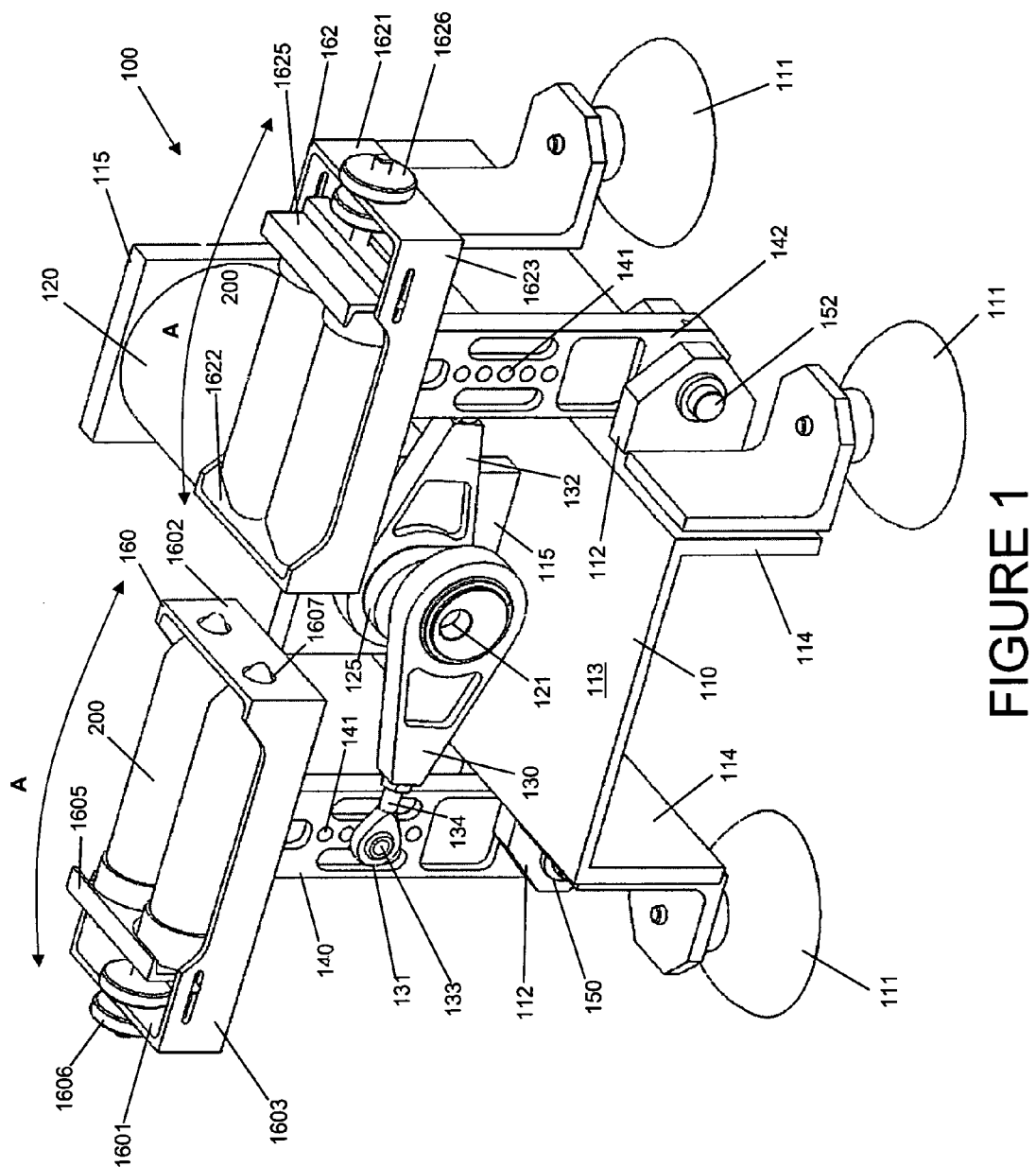
FIG. 1 is a front perspective view of a linear shaker according to certain aspects of an embodiment of the invention.
Figure 8:
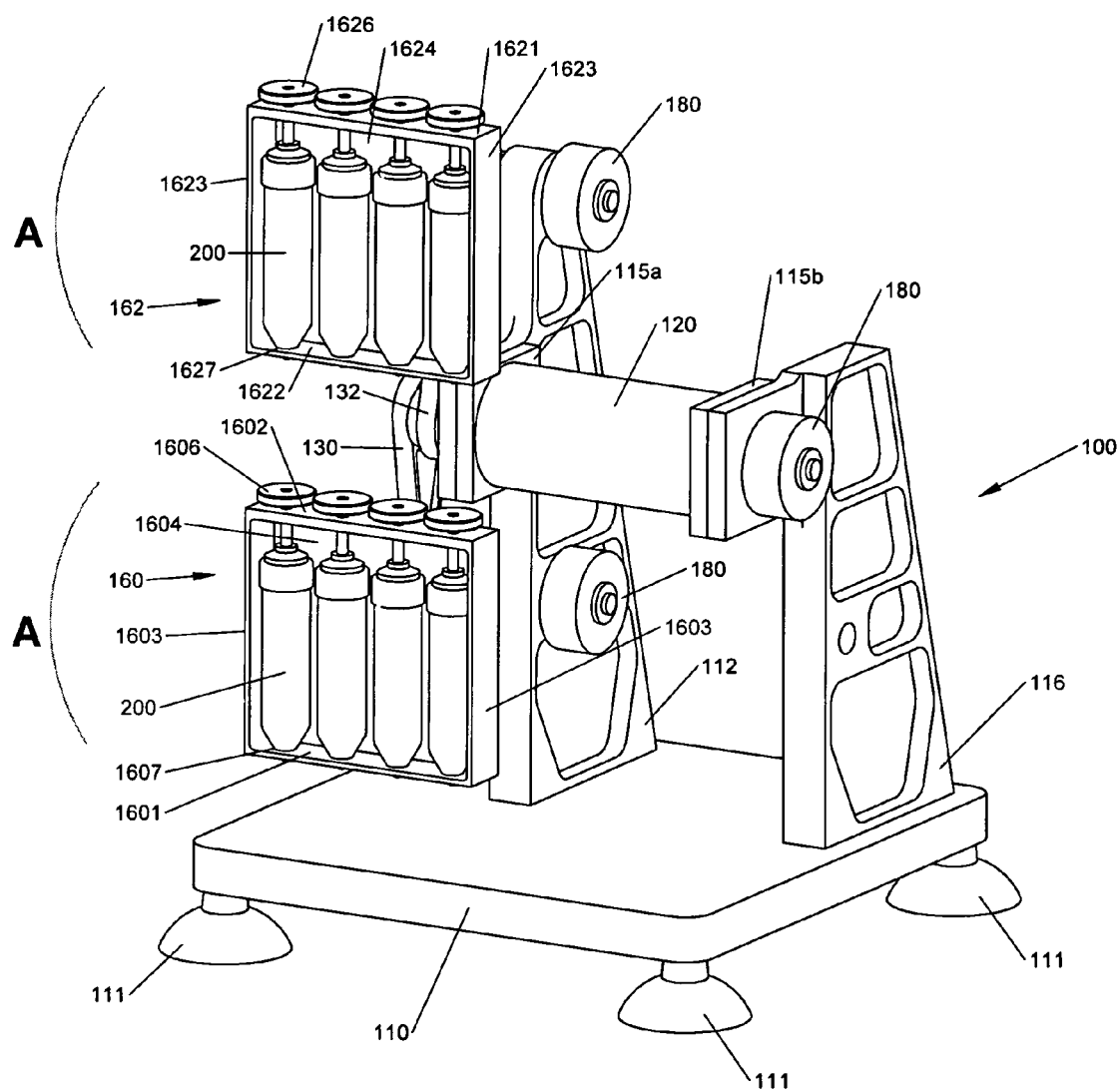
FIG. 8 is a front perspective view of a linear shaker according to further aspects of an embodiment of the invention.
Figure 9:
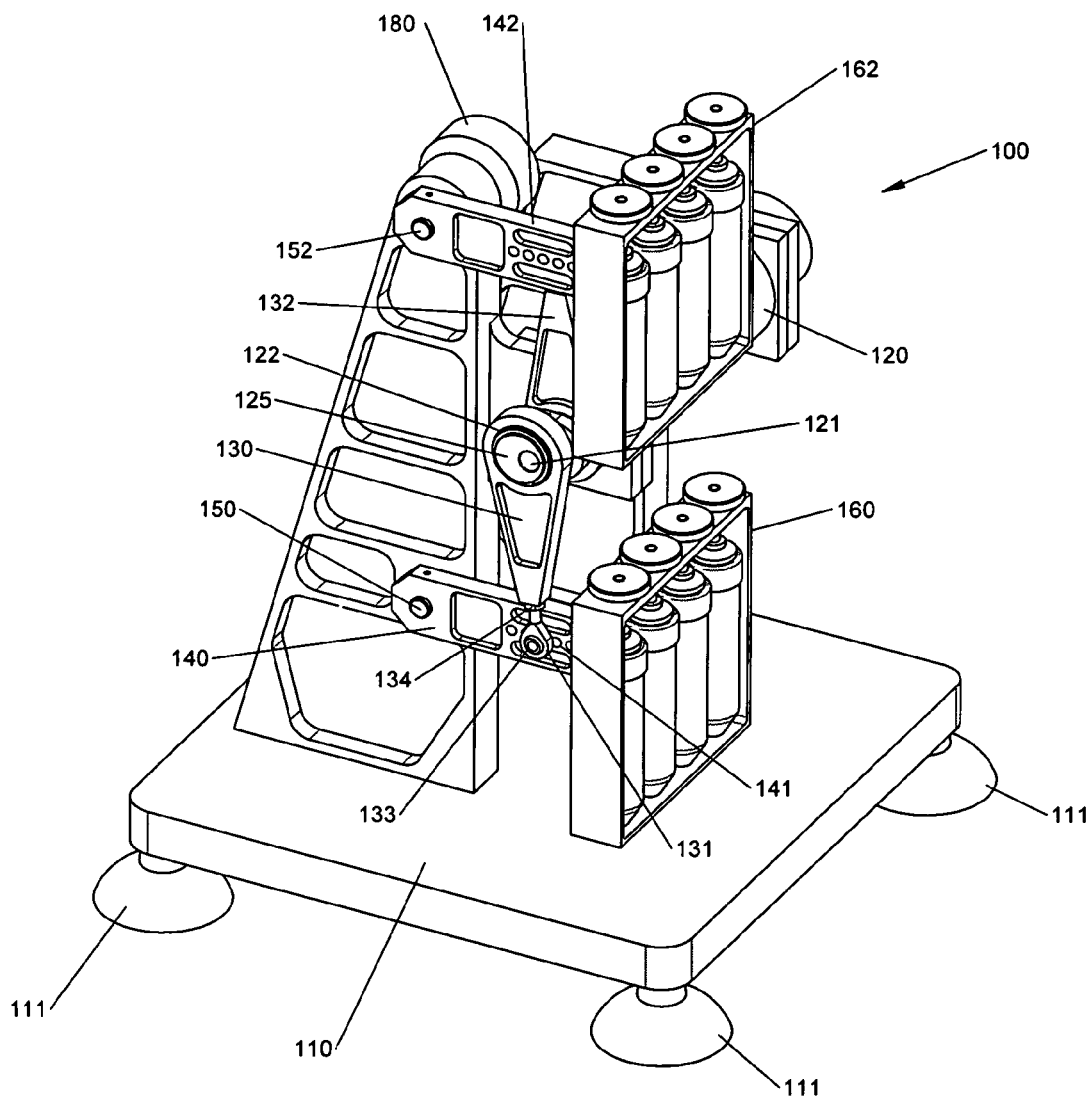
FIG. 9 is a side perspective view of the linear shaker of FIG. 9.

First, by way of summary of certain aspects of the invention, and with particular reference to FIGS. 1, 8, and 9, a shaker 100 is provided having a base 110 and a variable speed electric motor 120 preferably rigidly attached to base 110. Electric motor 120 is provided a drive shaft extending from one end of electric motor 120 and connected to an eccentric crank shaft assembly 125 that rotates about the drive shaft when electric motor 120 is operated. Crank shaft 125 extends into a first end of each of two connecting arms 130 and 132. Connecting arms 130 and 132 are mounted to crank shaft 125 such that they generally point away from one another in opposite directions. The opposite end of each of connecting arms 130 and 132 are adjustably attached to pivot arms 140 and 142. Pivot arms 140 and 142 are pivotably mounted to base 110 at pivot connections 150 and 152, respectively, and at their opposite ends to specimen trays 160 and 162, respectively. Thus, when electric motor 120 is operated, the rotation of eccentric crank shaft 125 causes connecting arms 130 and 132 to cyclically push and pull pivot arms 140 and 142, causing each of them to pivot about their respective pivot connections 150 and 152, and in turn cause each of specimen trays 160 and 162 to travel through a slightly arcuate but near-linear path A, thus shaking specimens positioned within specimen trays 160 and 162 through a back and forth, nearly linear shaking motion.

Figure 2:
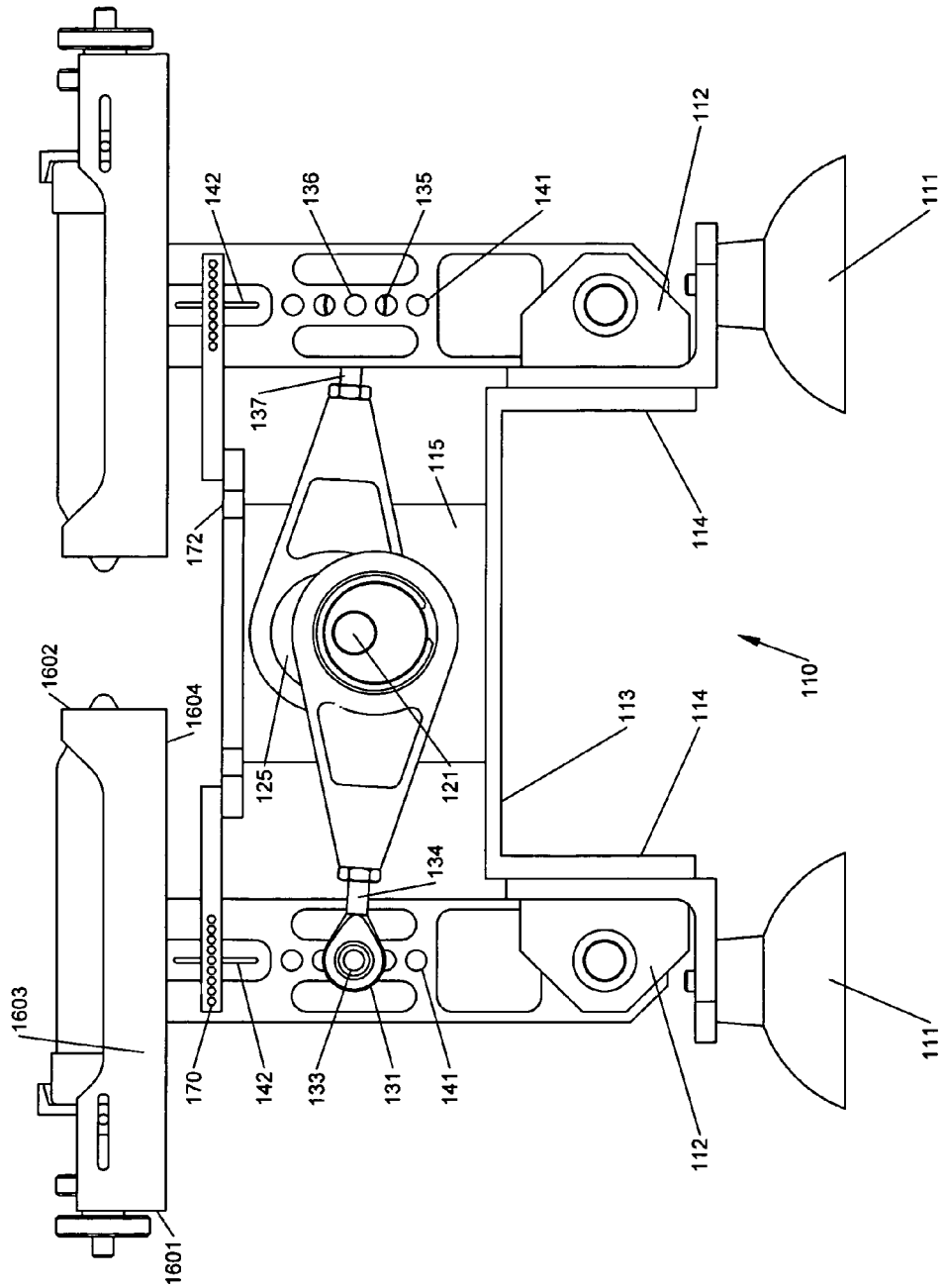
FIG. 2 is a front view of the linear shaker of FIG. 1 and including an encoding device.

More particularly, and with reference to FIGS. 1 and 2, shaker 100 may be configured so as to cause near-linear path A (through which specimen trays 160 and 162 travel) to be nearly horizontal. In this configuration, base 110 is provided a plurality of flexible feet 111, such as (by way of non-limiting example) rubber or generally elastomeric suction cups configured to hold shaker 100 in its intended position on a smooth, flat surface. Base 110 is also provided pivot mounting brackets 112, each of which is configured to receive pivot connections 150 and 152. More particularly, a pivot pin extends through each of pivot mounting brackets 112 and a lower end of each pivot arm 140 and 142, thus allowing each pivot arm 140 and 142 to pivot about its pivot connection without separating from base 110. Preferably, base 110 has a generally planar top wall 113 and two generally vertical walls 114, and each pivot mounting bracket 112 is positioned on an outside face of one of the vertical walls 114. Base 110 also includes motor support walls 115 extending upward from the top wall 113 of base 110 and configured to mount electric motor 120 between them. This, in turn, positions the motor assembly and specimen trays 160 and 162 vertically above base 110 allowing easy access by a system operator.

Figure 3:
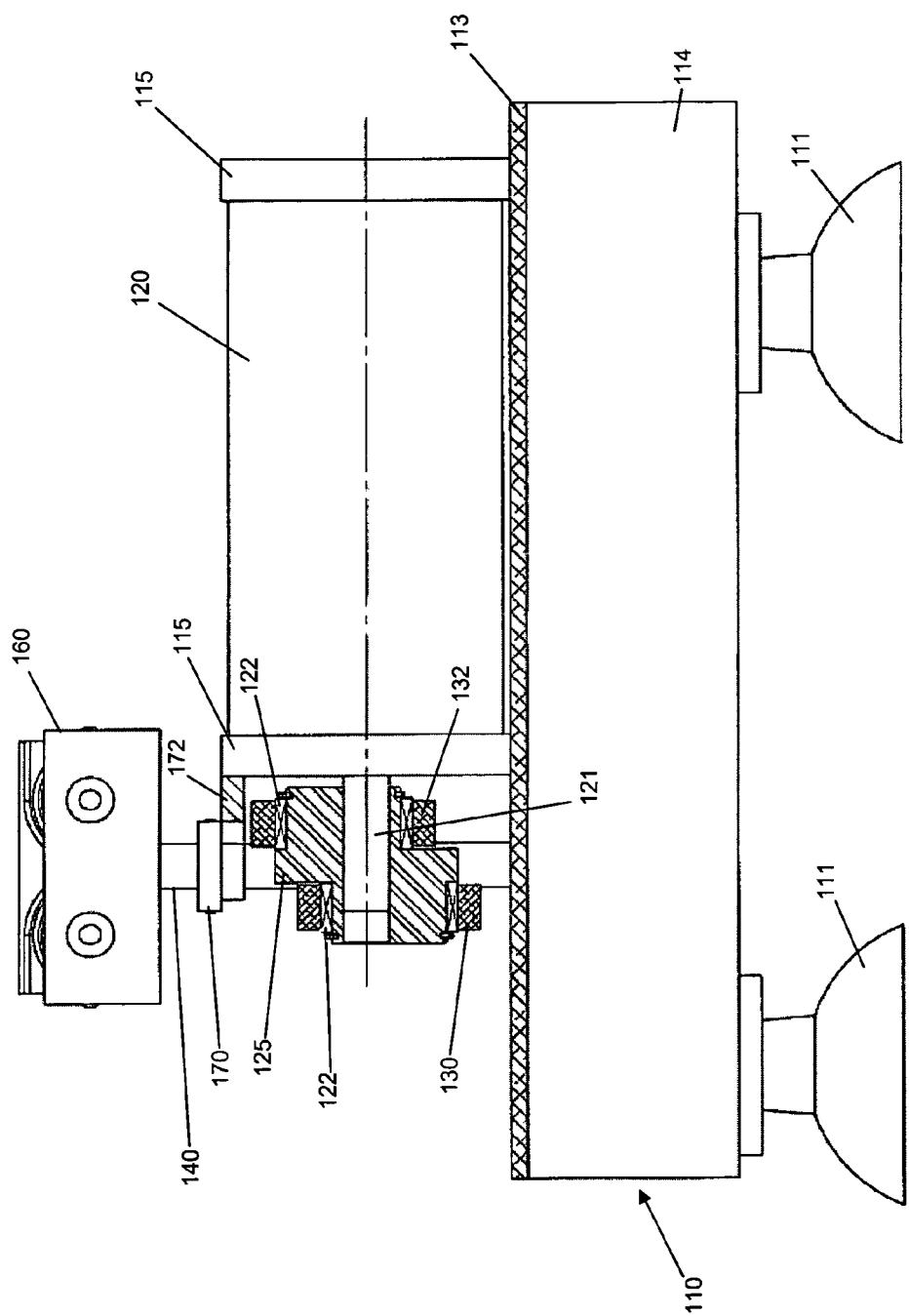
FIG. 3 is a side, partial cross-sectional view of the linear shaker of FIG. 1.

Variable speed electric motor 120 is positioned between and affixed to motor support walls 115. As shown in FIG. 3, a drive shaft 121 extends from electric motor 120 through wall 115 and into eccentric crank shaft assembly 125, and is affixed to crank shaft assembly 125 such that rotation of drive shaft 121 likewise causes rotation of crank shaft assembly 125 about drive shaft 121. A retaining ring 122 is preferably situated between crank shaft assembly 125 and each connecting arm 130 and 132 allowing relative pivoting of each connecting arm about crank shaft assembly 125. While not shown, a SCR (Silicon-Controlled-Rectifier) unit of standard configuration may be provided and electrically connected to motor 120 so as to allow electric motor 120 to operate at variable speeds as an operator may see fit for particular mixing operations. Alternatively, other drive and/or control mechanisms may be provided without departing from the spirit and scope of the invention, such as (by way of non-limiting example) a mechanical variable speed pulley assembly.

As mentioned above, a first end of each of connecting arms 130 and 132 is configured to receive a retaining ring 122 which pivotably mounts each of connecting arms 130 and 132 to eccentric crank shaft assembly 125. An opposite end of connecting arm 130 terminates in a head 131 that is pivotably attached to preferably a front side of pivot arm 140 with a pivot pin 133. Head 131 is attached to a rod 134, the position of which may be adjusted so as to vary the distance of head 131 from the main body portion of connecting arm 130. Pivot arm 140 is likewise provided a plurality of openings 141 configured to receive pivot pin 133, such that the position of head 131 with respect to pivot arm 140 may be adjusted, in turn adjusting the stroke of connecting arm 130, and in turn the total stroke of near linear path A achieved by specimen tray 160.

Similarly, an opposite end of connecting arm 132 terminates in a head 135 that is pivotably attached to preferably a back side of pivot arm 142 with a pivot pin 136. Head 135 is attached to a rod 137, the position of which may be adjusted so as to vary the distance of head 135 from the main body portion of connecting arm 132. Pivot arm 142 is likewise provided a plurality of openings 141 configured to receive pivot pin 136, such that the position of head 135 with respect to pivot arm 142 may be adjusted, in turn adjusting the stroke of connecting arm 132, and in turn the total stroke of near linear path A achieved by specimen tray 162.

As mentioned briefly above, pivot arm 140 is pivotably attached at one end to base 110, and particularly to one of pivot mounting brackets 112, with a pivot connection 150 comprising a pivot pin extending through mounting bracket 112 and pivot arm 140. The opposite end of pivot arm 140 is affixed to specimen tray 160, such that movement of pivot arm 140 about pivot connection 150 causes specimen tray 160 to travel through near-linear path A. Similarly, pivot arm 142 is pivotably attached at one end to base 110, and particularly to the other one of pivot mounting brackets 112, with a pivot connection 152 comprising a pivot pin extending through mounting bracket 112 and pivot arm 142. The opposite end of pivot arm 142 is affixed to specimen tray 162, such that movement of pivot arm 142 about pivot connection 152 causes specimen tray 162 to travel through near-linear path A.

Specimen tray 160 is preferably rigidly attached to the free end of pivot arm 140. Specimen tray 160 is configured as an open, generally rectangular tray having an outer wall 1601, an inner wall 1602, two side walls 1603 connecting outer wall 1601 and 1602, and a bottom wall 1604. A slider plate 1605 is positioned within specimen tray 160, and is attached to a threaded adjustment knob assembly 1606 that allows the position of slider plate 1605 within specimen tray 160 to be modified and locked in place. Thus, a specimen container 200, such as (by way of non-limiting example) a 50 ml test tube, may be positioned within specimen tray 160 and slider plate may be compressed against a top end of the specimen container 200 to hold the specimen container 200 in place during a mixing operation. Optionally, openings 1607 may be provided in inner wall 1602 to receive and properly position a bottom end of specimen container 200.

Similarly, specimen tray 162 is preferably rigidly attached to the free end of pivot arm 142. Specimen tray 162 is configured as an open, generally rectangular tray having an outer wall 1621, an inner wall 1622, two side walls 1623 connecting outer wall 1601 and 1602, and a bottom wall 1624. A slider plate 1625 is positioned within specimen tray 162, and is attached to a threaded adjustment knob assembly 1626 that allows the position of slider plate 1625 within specimen tray 162 to be modified and locked in place. Thus, a specimen container 200 may again be positioned within specimen tray 162 and slider plate 1625 may be compressed against a top end of the specimen container 200 to hold the specimen container 200 in place during a mixing operation. Optionally, openings 1627 may be provided in inner wall 1622 to receive and properly position a bottom end of specimen container 200.

Those of ordinary skill in the art will recognize that other positioning devices for receiving a properly positioning a variety of specimen containers of varied configuration may likewise be provided to suit particular mixing operations without departing from the spirit and scope of the invention.

Figure 4:
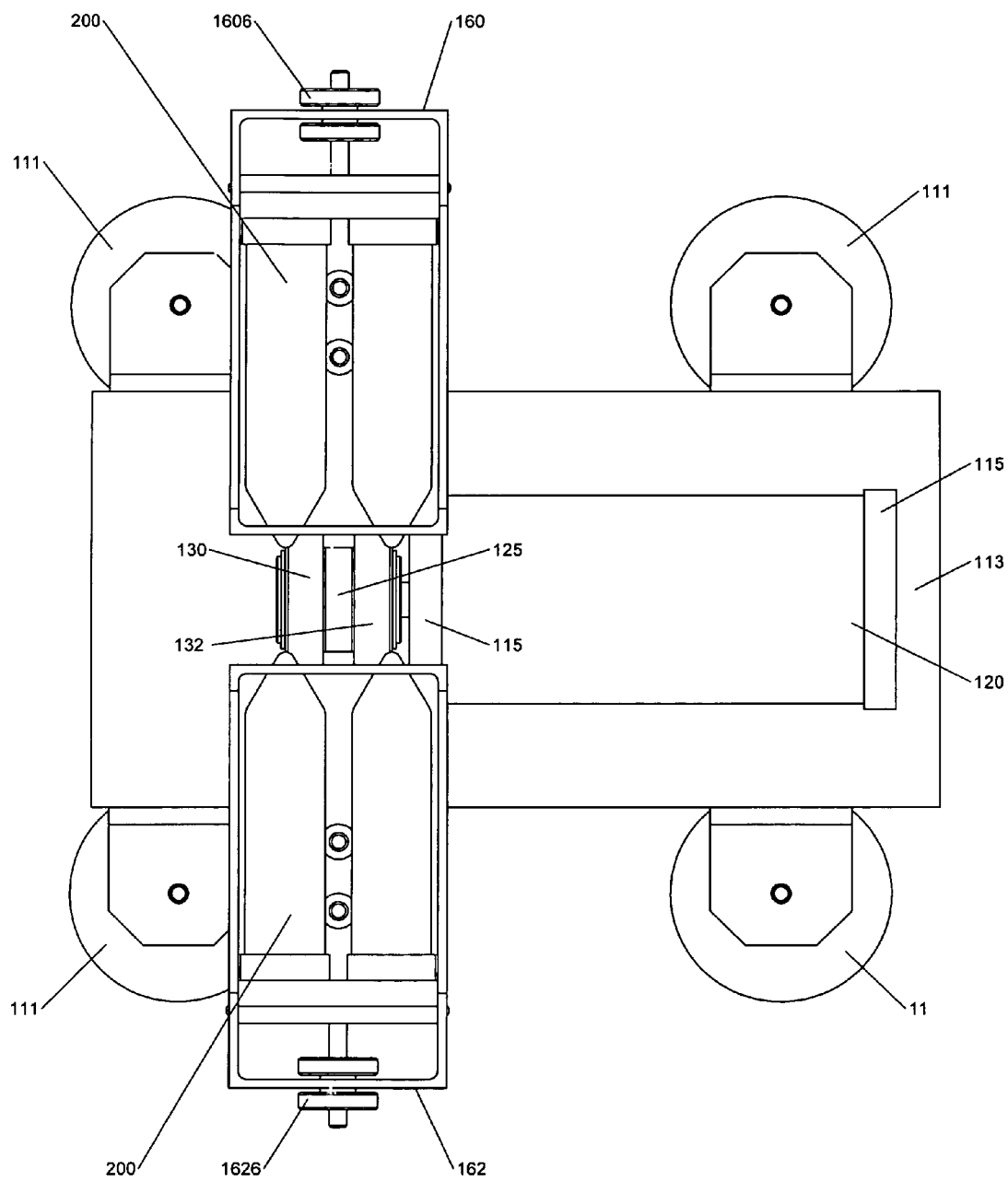
FIG. 4 is a top view of the linear shaker of FIG. 1.
Figure 5:
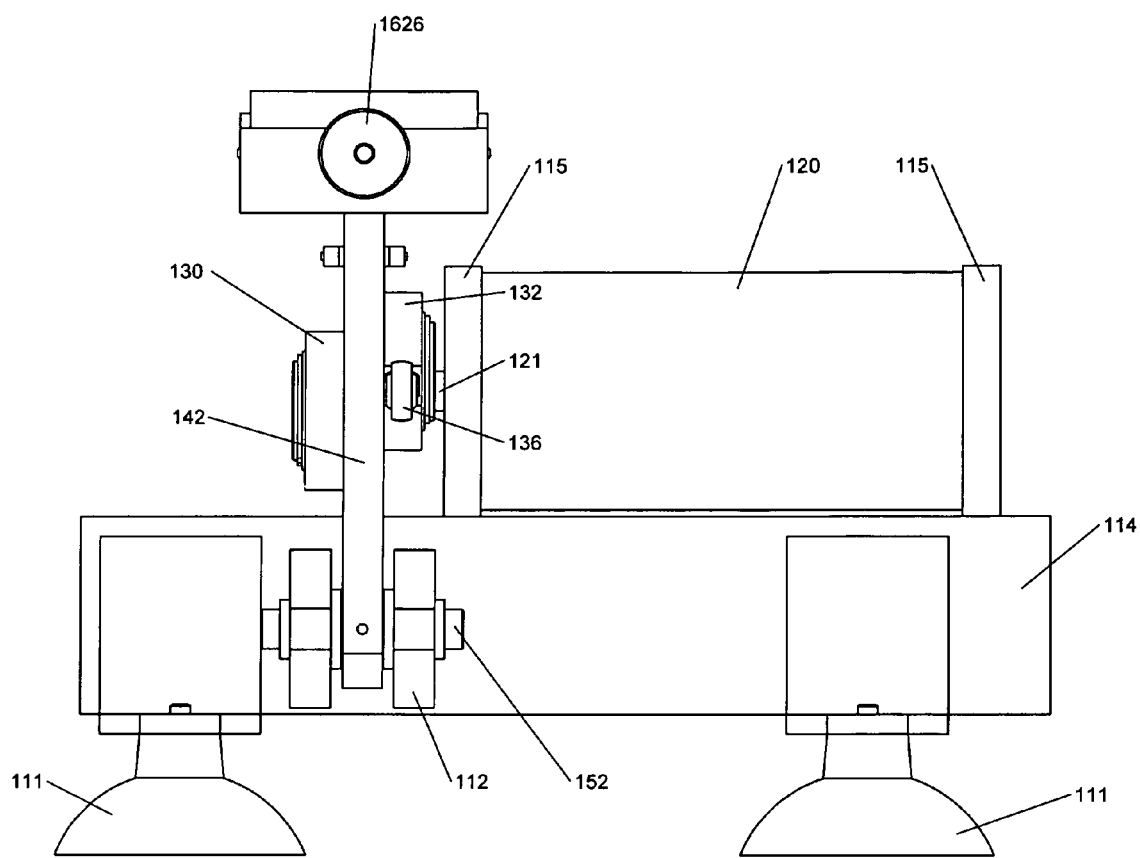
FIG. 5 is a side view of the linear shaker of FIG. 1.
Figure 6:
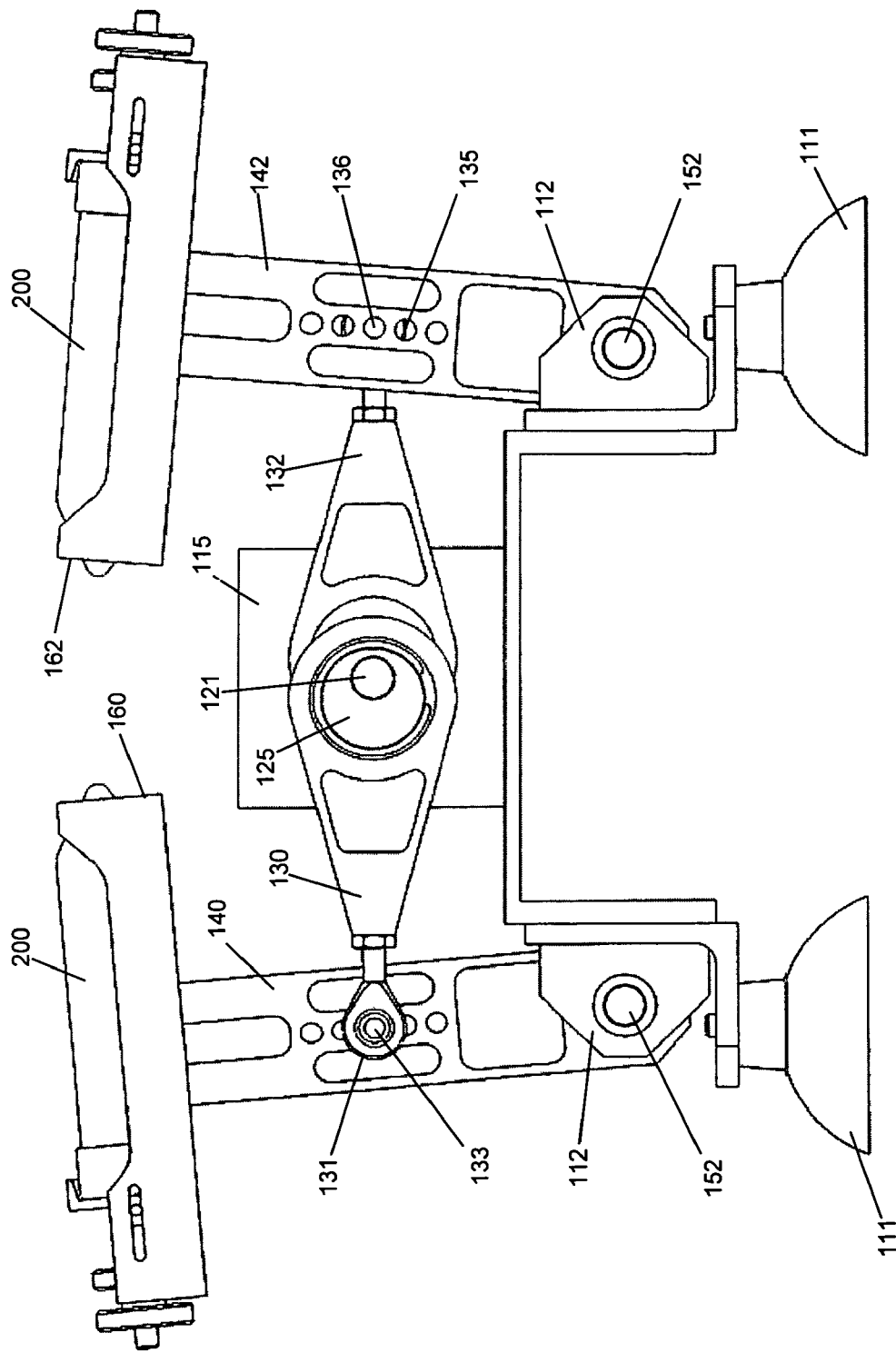
FIG. 6 is a front view of the linear shaker of FIG. 1.

FIGS. 4 and 5 show top and side views of the linear shaker 100 described above. Likewise, FIG. 6 provides a front view of linear shaker 100 with each of specimen trays 160 and 162 at the maximum distant point of near-linear arcuate path A during a mixing operation.

Figure 7:
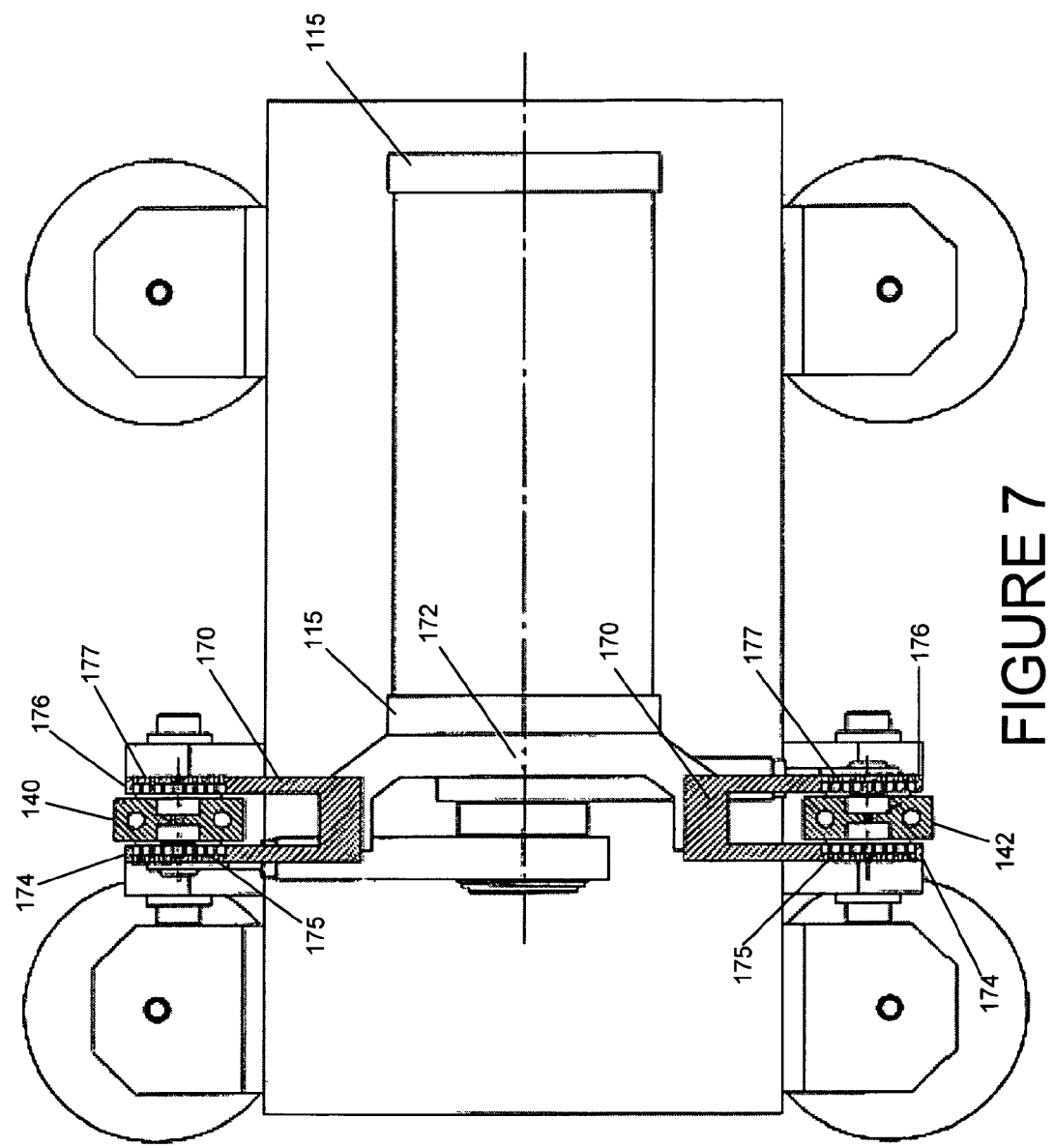
FIG. 7 is a top, partial cross-sectional view of the linear shaker of FIG. 2.

Optionally, and as shown in FIGS. 2 and 7, an encoder 170, and more preferably an optical encoder, may be provided to determine the maximum stroke achieved by each of specimen trays 160 and 162. The measurement of such maximum stroke may be compared to the speed of variable speed electric motor 120 if an operator desires to limit the maximum shaking velocity if the adjustable stroke is too great. This feature may be used to limit excessive vibratory forces from being encountered during a mixing operation. With particular reference to FIGS. 2 and 7, encoder 170 is affixed to a bracket 172 positioned at the top of the front motor support wall 15. Each detection head of encoder 170 has an opening through which each of pivot arms 140 and 142 travel, a first arm 174 including a plurality of light emitters 175, such as light emitting diodes, and a second arm 176 including a plurality of light receptors 177, such as photo diode receptors. As best seen in FIG. 2, when an encoder is utilized, each of pivot arms 140 and 142 are preferably provided a slit 142 allowing light emitted from emitters 175 to be received by an associated receptor 177, such that the instantaneous position of pivot arms 140 and 142 may be determined and a calculation made of the maximum stroke that is being achieved at that time.

Figure 10:
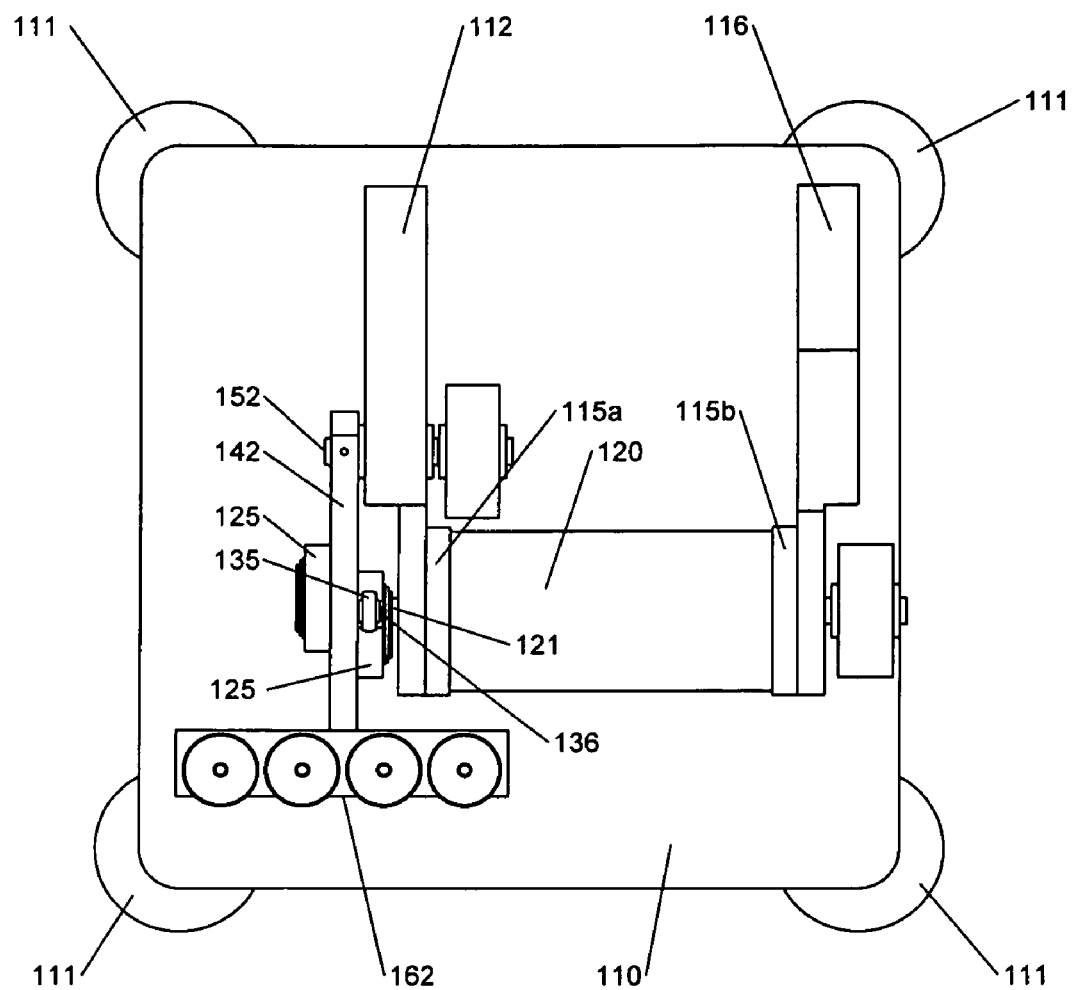
FIG. 10 is a top view of the linear shaker of FIG. 9.

As shown in FIGS. 8, 9, and 10, linear shaker 100 may be configured so as to cause near-linear path A (through which specimen trays 160 and 162 travel) to be nearly vertical. In this configuration, base 110 is again provided a plurality of flexible feet 111, such as (by way of non-limiting example) rubber or generally elastomeric suction cups configured to hold shaker 100 in its intended position on a smooth, flat surface. Base 110 is also provided a pivot mounting bracket 112 configured to receive pivot connections 150 and 152. More particularly, two pivot pins extend through pivot mounting bracket 112 at positions that are horizontally aligned and vertically separated from one another. Each such pivot pin likewise extends through a pivoting end of each of pivot arm 140 and 142, thus allowing each pivot arm 140 and 142 to pivot about its pivot connection without separating from base 110. Base 110 also preferably includes a motor support truss 116 supporting a first motor support wall 115a and configured to mount one end of electric motor 120. A second motor support wall 115b is preferably affixed to pivot mounting bracket 112, such that variable speed electric motor 120 is mounted between first motor support wall 115a and second motor support wall 115b. This assembly, again, positions the motor assembly and specimen trays 160 and 162 vertically above base 110 allowing easy access by a system operator.

With continued reference to FIGS. 8 through 10, variable speed electric motor 120 is positioned between and affixed to motor support walls 115a and 115b. As described in greater detail above, a drive shaft 121 extends from electric motor 120 through wall 115b and into eccentric crank shaft assembly 125, and is affixed to crank shaft assembly 125 such that rotation of drive shaft 121 likewise causes rotation of crank shaft assembly 125 about drive shaft 121. A retaining ring 122 is again preferably situated between crank shaft assembly 125 and each connecting arm 130 and 132 allowing relative pivoting of each connecting arm about crank shaft assembly 125. Once again, an SCR (Silicon-Controlled-Rectifier) unit of standard configuration may be provided and electrically connected to motor 120 so as to allow electric motor 120 to operate at variable speeds as an operator may see fit for particular mixing operations. Alternatively, other drive and/or control mechanisms may be provided without departing from the spirit and scope of the invention, such as (by way of non-limiting example) a mechanical variable speed pulley assembly.

Also, as best seen in FIG. 9, a first end of each of connecting arms 130 and 132 is configured to receive bearing disc 122 which pivotably mounts each of connecting arms 130 and 132 to eccentric crank shaft assembly 125. An opposite end of connecting arm 130 terminates in a head 131 that is pivotably attached to preferably a front side of pivot arm 140 with a pivot pin 133. Head 131 is attached to a rod 134, the position of which may be adjusted so as to vary the distance of head 131 from the main body portion of connecting arm 130. Pivot arm 140 is likewise provided a plurality of openings 141 configured to receive pivot pin 133, such that the position of head 131 with respect to pivot arm 140 may be adjusted, in turn adjusting the stroke of connecting arm 130, and in turn the total stroke of near linear path A achieved by specimen tray 160.

Similarly, and as best seen in FIG. 10, an opposite end of connecting arm 132 terminates in a head 135 that is pivotably attached to preferably a back side of pivot arm 142 with a pivot pin 136. Once again and as described above, head 135 is attached to a rod, the position of which may be adjusted so as to vary the distance of head 135 from the main body portion of connecting arm 132. Pivot arm 142 is likewise provided a plurality of openings 141 configured to receive pivot pin 136, such that the position of head 135 with respect to pivot arm 142 may be adjusted, in turn adjusting the stroke of connecting arm 132, and in turn the total stroke of near linear path A achieved by specimen tray 162.

As described above and with continued reference to FIGS. 8-10, pivot arm 140 is pivotably attached at one end to base 110, and particularly to pivot mounting bracket 112, with a pivot connection 150 comprising a pivot pin extending through pivot mounting bracket 112 and pivot arm 140. The opposite end of pivot arm 140 is affixed to specimen tray 160, such that movement of pivot arm 140 about pivot connection 150 causes specimen tray 160 to travel through near-linear path A. Similarly, pivot arm 142 is pivotably attached at one end to base 110, and particularly to pivot mounting bracket 112 at a point above the point of attachment of pivot arm 140, with a pivot connection 152 comprising a pivot pin extending through pivot mounting bracket 112 and pivot arm 142. The opposite end of pivot arm 142 is affixed to specimen tray 162, such that movement of pivot arm 142 about pivot connection 152 causes specimen tray 162 to travel through near-linear path A.

As shown in FIGS. 8-10, specimen tray 160 is again preferably rigidly attached to the free end of pivot arm 140, and is configured as an open, generally rectangular tray having an outer wall 1601, an inner wall 1602, two side walls 1603 connecting outer wall 1601 and 1602, and a bottom wall 1604. While a slider plate as described above may be used, alternatively threaded adjustment knob assemblies 1606 may be provided for each specimen container 200 that may clamp each specimen container 200 within tray 160 and, once clamped, remain locked in place. Thus, specimen containers 200, such as (by way of non-limiting example) a plurality of 50 ml test tubes, may be positioned within specimen tray 160 and adjustment knob assemblies 1606 may be compressed against the top ends of the specimen containers 200 to hold the specimen containers 200 in place during a mixing operation. Optionally, openings may be provided in outer wall 1601 to receive and properly position a bottom end of specimen container 200.

Similarly, specimen tray 162 is again preferably rigidly attached to the free end of pivot arm 142, and is configured as an open, generally rectangular tray having an outer wall 1621, an inner wall 1622, two side walls 1623 connecting outer wall 1621 and 1622, and a bottom wall 1624. As with specimen tray 160, threaded adjustment knob assemblies 1626 may again be provided for each specimen container 200 that may clamp each specimen container 200 within tray 162 and, once clamped, remain locked in place. Thus, specimen containers 200, such as (by way of non-limiting example) a plurality of 50 ml test tubes, may be positioned within specimen tray 162 and adjustment knob assemblies 1626 may be compressed against the top ends of the specimen containers 200 to hold the specimen containers 200 in place during a mixing operation. Optionally, openings may be provided in inner wall 1622 to receive and properly position a bottom end of specimen container 200.

Once again, those of ordinary skill in the art will recognize that other positioning devices for receiving and properly positioning a variety of specimen containers of varied configuration may likewise be provided to suit particular mixing operations without departing from the spirit and scope of the invention.

Optionally, and similar to the configuration described above with regard to FIGS. 2 and 7, rotary encoders 180 (configured to measure the angular displacement of each of pivot arms 140 and 142) may again be provided to determine the maximum stroke achieved by each of specimen trays 160 and 162. The measurement of such maximum stroke may again be compared to the speed of variable speed electric motor 120 if an operator desires to limit the maximum speed if the adjustable stroke is too great. This feature may be used to limit excessive vibratory forces from being encountered during a mixing operation, as well as optimizing the mixing and/or macerating procedure.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

I claim:

1. A specimen shaker comprising:
    a base having a first pivot connection and a second pivot connection;
    a first pivot arm pivotably connected to said base at said first pivot connection, said first pivot arm having a first end located adjacent said first pivot connection and a second end opposite said first end;
    a second pivot arm pivotably connected to said base at said second pivot connection, said second pivot arm having a first end located adjacent said second pivot connection and a second end opposite said first end;
    a first specimen holder attached to said first pivot arm at said second end of said first pivot arm and configured to shake a specimen contained therein in a direction generally perpendicular to said first pivot arm;
    a second specimen holder attached to said second pivot arm at said second end of said second pivot arm and configured to shake a specimen contained therein in a direction generally perpendicular to said second pivot arm;
    a drive affixed to said base and having a crank shaft;
    a first connecting arm extending between said crank shaft and said first pivot arm; and
    a second connecting arm extending between said crank shaft and said second pivot arm;
    wherein rotation of said crank shaft causes each of said first pivot arm and said second pivot arm to pivot about said first pivot connection and said second pivot connection, respectively.

2. The specimen shaker of claim 1, wherein each of said first and second specimen holders further comprise:
    a generally rectangular tray mounted on said free end of each of said first and second pivot arms; and
    a plurality of hollow specimen containers mounted within each said tray, each said specimen container configured to removably receive a specimen therein, and each said cylinder having a mixing aid device therein configured to move within said cylinder as said first and second pivot arms are pivoted about their respective first and second pivot connections.

3. The specimen shaker of claim 2, wherein each of said first and second specimen holders further comprises at least one adjustment knob assembly configured to adjustably push against a top end of said specimen containers when said specimen containers are positioned within each said specimen holder so as to removably hold said specimen containers within each said specimen holder during a mixing operation.

4. The specimen shaker of claim 1, wherein said first connecting arm is pivotably attached to said first pivot arm, and said second connecting arm is pivotably attached to said second pivot arm.

5. The specimen shaker of claim 4, wherein said first pivot arm further comprises a plurality of first openings configured to receive a first pivot pin, and said second pivot arm further comprises a plurality of second openings configured to receive a second pivot pin, and further wherein said first pivot pin extends through said first connecting arm and through one of said first openings to pivotably attach said first connecting arm to said first pivot arm, and said second pivot pin extends through said second connecting arm and through one of said second openings to pivotably attach said second connecting arm to said second pivot arm.

6. The specimen shaker of claim 1, wherein said drive further comprises a variable speed electric motor having a drive shaft that engages said crank shaft so as to eccentrically drive each of said first and second connecting arms.

7. The specimen shaker of claim 1, further comprising an encoder configured to measure a maximum stroke of each of said first and second specimen trays.

8. The specimen shaker of claim 1, wherein said shaker is configured to move each of said first and second specimen trays in a nearly linear direction that is approximately horizontal.

9. The specimen shaker of claim 1, wherein said shaker is configured to move each of said first and second specimen trays in a nearly linear direction that is approximately vertical.

* * * * *